United States Patent [19]

Feaster

[11] Patent Number: 4,842,600
[45] Date of Patent: Jun. 27, 1989

[54] INTRAOCULAR LENS WITH VARIABLE CIRCUMFERENCE ENCIRCLING HAPTIC

[76] Inventor: Fred T. Feaster, 800 8th Ave., Suite 234, Fort Worth, Tex. 76104

[21] Appl. No.: 169,412

[22] Filed: Mar. 17, 1988

[51] Int. Cl.⁴ ............................................. A61F 2/16
[52] U.S. Cl. ............................................. 623/6
[58] Field of Search ..................................... 623/6

[56] References Cited

U.S. PATENT DOCUMENTS

| 4,251,887 | 2/1981 | Anis | 623/6 |
| 4,418,431 | 12/1983 | Feaster | 623/6 |
| 4,434,515 | 3/1984 | Poler | 623/6 |
| 4,494,254 | 1/1985 | Lopez | 623/6 |

FOREIGN PATENT DOCUMENTS 667206  6/1979  U.S.S.R. ................................. 623/6

OTHER PUBLICATIONS

New Concepts in Circular Posterior Chamber Lenses, Ocular Surgery News, Oct. 1, 1987, pp. 16–18.

*Primary Examiner*—Ronald L. Frinks
*Attorney, Agent, or Firm*—Arthur F. Zobal

[57] ABSTRACT

The intraocular lens includes a lens body having a haptic for supporting the lens body in a human eye. The haptic includes a surrounding portion adapted to engage the tissue of a human eye and which extends at least 360° around the axis of the lens body at a position spaced outward from the periphery thereof. The haptic comprises a single haptic member in one embodiment and a plurality of haptic members in another embodiment each comprising an inner connecting portion having its inner end joined to the periphery of the lens body and extending outward and then around or partially around the axis of the lens body forming the surrounding portion and having an outer portion with an outer end portion. In the case of a single haptic member the haptic member overlaps itself. In the case of a plurality of haptic members each, each haptic member has an outer portion with its outer end portion which overlaps an adjacent portion of another haptic member. A loop or wound or twisted portion is joined to the outer end portion of each haptic member with the inner adjacent portion of the single haptic member or the adjacent inner portion of another haptic member extending through the loop or wound portion such that the outer end portion may be moved along the adjacent portion to decrease or expand the circumference of the surrounding portion of the haptic.

20 Claims, 5 Drawing Sheets

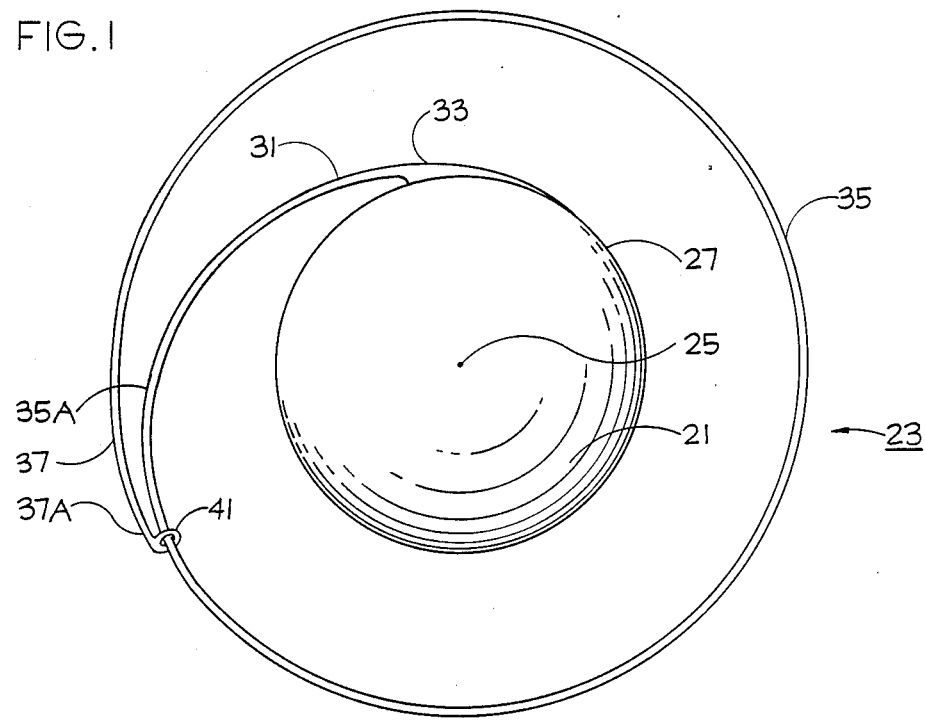
FIG. 1
FIG. 2
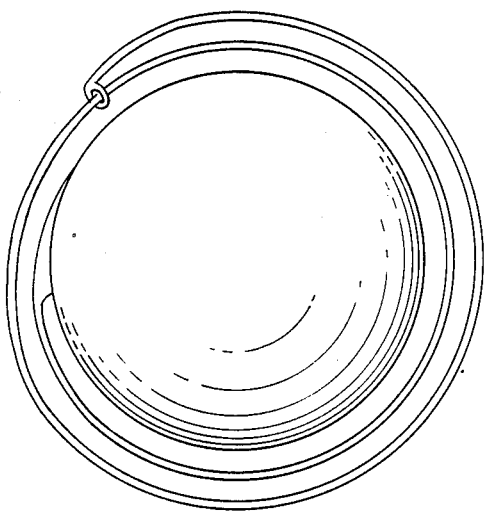
FIG. 4
FIG. 3

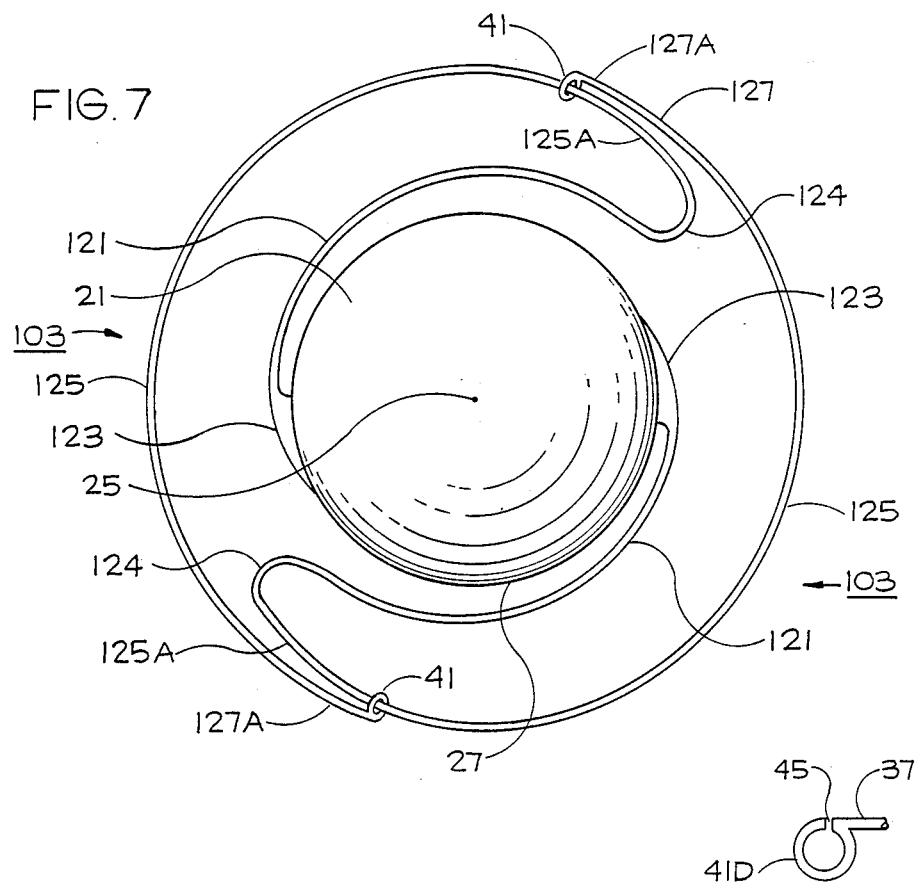
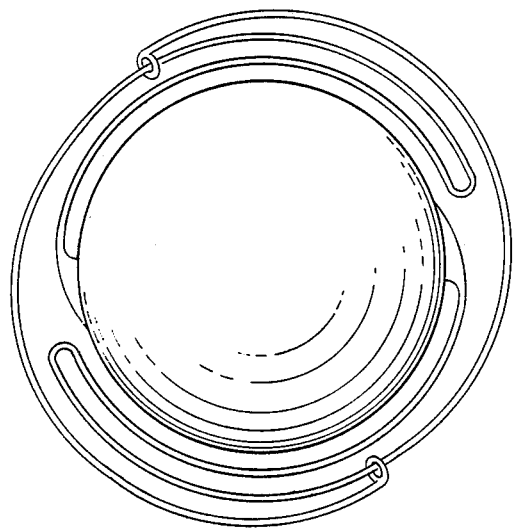

INTRAOCULAR LENS WITH VARIABLE CIRCUMFERENCE ENCIRCLING HAPTIC

BACKGROUND OF THE INVENTION

1. Field of the Invention

The invention relates to an intraocular lens for the human eye.

2. Description of the Prior Art

As intraocular lens implantation surgery has evolved, it has become clear that at this time, the most desirable location for an intraocular lens to be placed within the eye is in the posterior chamber. Furthermore, of the two locations available within the posterior chamber for placement of the intraocular lens, namely the ciliary sulcus or the capsular bag, it has been found most desirable to place the intraocular lens completely within the capsular bag. That is to say, the entire intraocular lens, including the optic and the haptic fixation members of the intraocular lens, is placed within the capsular "bag", the retained membranous capsular envelope which at one time contained the cataractous lens and is left behind as a result of an extracapsular or endocapsular cataract extraction. Ideally, the entire intraocular lens is placed and contained within the remaining capsular bag. This is desirable because it has been observed through clinical and pathological observation that the capsule isolates and fixates the intraocular lens from the surrounding reactive tissues of the eye making the implanted lens less irritating to the eye and better tolerated and centered. Also, it has been observed that asymmetric placement of the lens implant partially within the capsular bag and partially out of the bag in the ciliary sulcus results in a higher incidence of decentration of the lens optic causing optical and visual problems. Therefore, for reasons of lens tolerance and centration, complete symmetrical placement of the intraocular lens within the capsular bag is very desirable. Furthermore, as will be explained below, it has been observed that a large area of peripheral haptic-capsule contact even to the point of complete continuous 360° circumferential contact is very desirable, if not the ideal. The historical developments in intraocular lens design leading to this conclusion are now presented.

The first modern intraocular lens design, which was developed and implanted by Ridley in November of 1949, was a posterior chamber intraocular lens intended for placement between the posterior capsule and the iris. Since that time, with some notable exceptions such as the designs of Pearce and Anis (U.S. Pat. No. 4,251,887), the more recent posterior chamber intraocular lens designs were also originally intended by their designers for placement within the posterior chamber in the ciliary sulcus, rather than within the capsular bag. The designs of Shearing, Sinskey, and Simcoe, which were developed in the latter half of the 1970's and the early 1980's when posterior chamber lens implantation was reintroduced and repopularized with modern surgical techniques, were initially intended for implantation in the ciliary sulcus. After clinical experience with posterior chamber implantation made it obvious that in-the-bag placement was more desirable than ciliary sulcus placement, these early posterior chamber intraocular lens designs intended originally for ciliary sulcus implantation were simply placed in the capsular bag without significant design modification. However, due to their limited design features, implantation, fixation, and centration within the capsular bag have been less than ideal.

It has become obvious from further clinical and pathological studies of lenses placed within the capsular bag that a large area of peripheral haptic-capsular contact is desirable for fixation and centration. This is in direct contrast to the earlier ciliary sulcus lens designs mentioned above which, due to the reactive nature of the ciliary sulcus tissue, strived for small rather than large areas of tissue contact to minimize ocular inflammation and thereby maximize ocular tolerance of the implant. It is now believed by some of the most respected investigators in the field of intraocular design, such as Apple, Galand and Anis, that the ideal in-the-bag intraocular lens design should incorporate the feature of continuous 360° circumferential peripheral haptic-capsular contact for centration. This complete circumferential contact would then virtually eliminate any problems with decentration due to asymmetric contracture of the capsule postoperatively.

With modern intraocular lens production technology, several new design concepts incorporating continuous 360° circumferential peripheral capsular contact have been developed and promoted, including the Galand disc lens and several designs by Anis. The disadvantage of the Galand disc lens is that its one-piece configuration is rigid and thereby requires a larger incision for implantation, both at the corneo-scleral limbus and in the capsular bag. Its rigidity threatens to tear or split the capsular incision during implantation resulting in serious clinical problems including vitreous loss and aborting of the posterior chamber implantation. These clinical problems have in fact been encountered resulting in attempts to modify the lens design by surrounding the central optic with a solid yet soft flexible material such as Silicone which might have less tendency to tear the delicate lens capsule during implantation. However, fixation and centration with this soft rim modification has been poor due to bending of the peripheral Silicone rim by the capsular contraction previously mentioned.

Anis has attempted to evolve the total circumferential contact design concept by developing designs which have 360° capsular contact comprising a central optic joined to an outer circular circumferential ring or ring and partial plate. The advantage of this design is that it adds considerable flexibility, allows implantation through a smaller incision, and is less threatening to the capsule during implantation. However, the outer circumferential haptic ring, though flexible, is nevertheless fixed in that the overall linear circumferential dimension is fixed and unchangeable. That is to say, even if the circumferential ring haptic is compressed or distorted such that the "radial" dimension in one direction is narrowed or diminished, because the overall circumference is fixed and incapable of changing, another "radial" dimension of the once circular and now distorted haptic must now enlarge. Decreasing the radial dimension of a fixed circumference in one direction necessarily requires an increase of the "radial" dimension in another direction to allow the overall fixed circumferential length to remain the same. It is understood that all discussion of haptic loop flexion refers to flexion in the plane of the optic, and assumes the materials involved (usually polymethylemethacrylate or prolene (polypropylene) are essentially nonelastic and cannot stretch.

All of the above mentioned lens designs, and in fact all currently known intraocular lenses, have one or more of the following design inadequacies that makes them less than the above-stated ideal:

1. Inability to provide full 360° circumferential capsular contact.
2. Inability to provide circumferential contact with an acceptable degree of flexibility.
3. Inability to adjust the overall linear dimension of the circumference (and radius) while still maintaining full 360° circumferential peripheral capsular contact.

The inability to adjust the overall linear dimension of the circumference and radius while still maintaining full 360° peripheral capsular contact is an especially significant and severe design limitation that puts any lens so designed at a noticeable disadvantage. This is because any such lens cannot conform to the different size capsular bags found in different eyes, or to a change in the capsular bag size resulting from capsular bag contraction within a given eye. Any lens that exhibits a fixed (although possibly flexible) overall effective circumferential and radial haptic dimension possesses this design flaw which limits its suitability for in-the-bag implantation.

To generalize further on this concept, it should be realized that it is not possible to create a 360° continuous capsular contact haptic configuration which will allow for a change in the overall effective linear dimension of its circumference and radius if all of the junctions between the haptics are such that the "inner" haptic (that haptic portion which joins the optic but does not contact the peripheral capsule for fixation) and the "outer" haptic (that haptic portion in contact with the peripheral capsule for fixation) are joined by fixed, nonmoveable junctions. To put this more succinctly, no intraocular lens in which all of the haptic-haptic junctions are fixed and nonmoveable can simultaneously display both the characteristics of:

1. Continuous 360° circumferential peripheral capsular contact, and
2. Variability in the linear dimension of that same circumference and corresponding radius. Stated another way, a lens must have at least one moveable haptic-haptic junction to display both of the above-mentioned characteristics.

As alluded to above, no known intraocular lens available possesses the features of both continuous 360° circumferential capsular contact and a variable dimension circumference. In any lens which has 360° continuous circumferential peripheral capsular contact by the haptic(s), if that circumference is to be variable, and in particular if it is to permit a reduction in the circumferential dimension, there must at some time occur a junction or even overlap of the haptics, and that junction or overlap must be nonfixed. The junction may occur between either "inner" and "outer" haptic portions as defined previously, or between two "outer" haptic portions. This moveable haptic-haptic junction has the property of allowing the haptics to overlap such that the effective circumferential dimension is adjustable and equal to the original circumference plus or minus the amount of overlap. Although one intraocular lens design has incorporated a moveable haptic-haptic design (U.S. Pat. No. 4,434,515), that lens design was a four point fixation style intended for anterior chamber rather than posterior chamber implantation, and in no way attempts or accomplishes 360° circumferential capsular contact. It is the failure of all other known intraocular lens designs with encircling haptics to have this moveable haptic-haptic junction that is their considerable drawback.

SUMMARY OF THE INVENTION

It is an object of the invention to provide an intraocular lens for the human eye having an encircling haptic means for continuous circumferential contact and which has means which allows its circumference and hence radial dimension to be varied for adaptation to different capsular bag sizes in different eyes or to allow for capsular bag shrinkage within the same eye.

The haptic means comprises at least one inner connecting portion having an inner end coupled to the periphery of the lens body and extending outward to a surrounding portion. The surrounding portion comprises at least one outer portion having an outer end portion and an adjacent portion located between said outer end portion and the axis of the lens body. Coupling means is provided for coupling said outer end portion and said adjacent portion together such that said outer end portion may be moved in an orderly fashion along said adjacent portion to decrease or expand the circumference of said surrounding portion of said haptic means.

The haptic means comprises a single haptic member in one embodiment and a plurality of haptic members in another embodiment each comprising an inner connecting portion having its inner end coupled to the periphery of the lens body and extending outward and then around or partially around the axis of the lens body forming said surrounding portion of said haptic means and having an outer portion with said outer end portion. In the case of a single haptic member, the haptic member overlaps itself. In the case of a plurality of haptic members, each haptic member has an outer portion with its outer end portion which overlaps an adjacent portion of another haptic member.

In the preferred embodiment, the coupling means is joined to the outer end portion of said outer portion of its haptic member and may comprise a loop or the outer end portion formed into a generally wound or twisted configuration with a passage with the adjacent portion of the haptic member or of the other haptic member extending through the opening or passage thereof. The adjacent haptic portion acts as a guide along which the outer portion can slide or otherwise move. By allowing the outer portion of the haptic to slide over its own inner portion or the adjacent portion of another haptic, an adjustable yet continuous circumference is achieved. The change in dimension of the circumference of the haptic is accomplished by this overlapping feature thereby changing the effective dimension of the haptic in contact with the peripheral capsule. This provides a mechanism to deal with the variability in dimension necessary to allow the haptic to enlarge or diminish its own circumference, as the case may be. Through this overlapping, the "redundancy" can be satisfactorily handled. The effective circumference in contact with the peripheral capsule can be varied and the variability in circumferential dimension is achieved while at the same time accomplishing a continuous 360° circumferential contact with the peripheral capsule.

It will be seen that if the haptics are properly shaped and configured relative to each other, they can, in addition to allowing for overlapping, mutually act as tracts or guides during haptic compression to direct and shape the haptic curvature such that the overlapping potential (and hence the dimensional changeability) can be maximized while maintaining the desired curvature.

BRIEF DESCRIPTION OF THE DRAWINGS

FIG. 1 is a plan view of one embodiment of the invention wherein the intraocular lens has a single haptic member.

FIG. 2 is a side view of FIG. 1 as seen from the right side thereof.

FIG. 3 illustrates the lens of FIG. 1 with its haptic in a compressed configuration.

FIG. 4 is an enlarged view of the coupling loop of the haptic of FIG. 1 showing more detail thereof.

FIG. 7 is a plan view of a lens with two haptic members with a different configuration.

FIG. 8 illustrates the lens of FIG. 7 with its haptic in a compressed configuration.

FIGS. 16 and 17 illustrate coupling loops similar to that of FIG. 4, with their gaps located at different positions.

DESCRIPTION OF THE PREFERRED EMBODIMENTS

Figure 5:
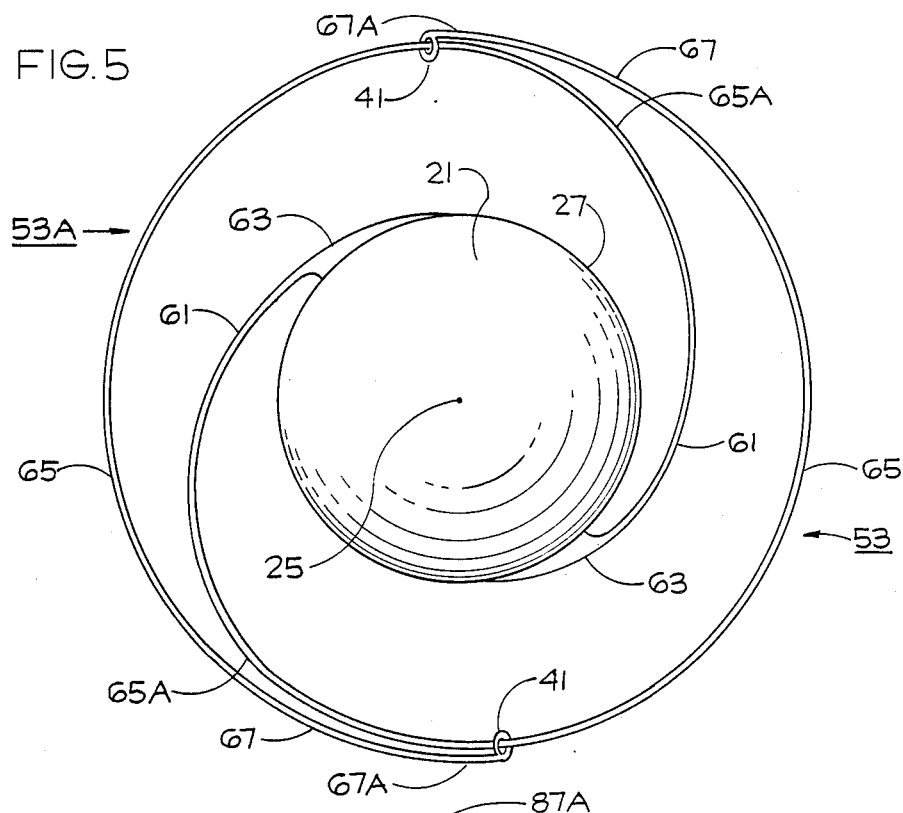
FIG. 5 is a plan view of another embodiment of the invention wherein the lens has two haptic members.

Referring now to FIGS. 1 through 4, there is shown an intraocular lens incorporating one embodiment of the haptic of the invention. The lens comprises a lens body or central optic portion 21 having a single haptic member 23. The lens body has a central axis 25 and an outer periphery 27. The haptic 23 is a spring type flexible member and comprises an inner connecting portion 31 having an inner end 33 joined to the periphery of the lens body 21 and extending outward to an outer surrounding portion 35 which extends at least 360° around the axis 25 and is spaced outward from the periphery of the lens body. The outer surrounding portion 35 has an outer end portion 37 which overlaps the adjacent inner portion 35A such that the adjacent inner portion 35A is located between the outer end portion 37 and the axis 25 and hence the periphery 27 of the lens body in the embodiment of FIGS. 1-4. The end 37A of the outer end portion 37 has a coupling loop 41 connected thereto with an opening 43 extending therethrough. The adjacent inner portion 35A extends freely through the opening 43 of the loop 41 such that the outer end portion 37 may move along the adjacent inner portion 35A to expand or decrease the dimension of the circumference of the surrounding portion 35 of the haptic which forms the peripheral contacting portion of the lens when inserted into the eye and holds the lens body centrally in place in the eye. As indicated above, preferably the lens will be located in the capsular bag of the eye with the surrounding portion 35 providing substantially 360° contact with the capsular bag. It can be understood that an external force compressing the surrounding haptic portion 35 will result in the loop 41 sliding over the adjacent inner portion 35A, which acts as a guide, thereby diminishing the overall effective circumferential dimension in contact with the peripheral capsule while still maintaining the circular contour of the haptic.

Referring to FIG. 4, the loop 41 has a slip or gap 45 formed therethrough in order to allow the adjacent haptic portion 35A to be located in the opening 43.

Referring now to FIG. 5, the intraocular lens comprises a lens body 21 having two identical haptic members 53. In FIG. 5, like components are identified by like reference numerals as disclosed in FIG. 1. The two haptic members 53 each comprises an inner connecting portion 61 having an inner end 63 coupled to the periphery 27 of the lens body 21 and extending outward to an outer surrounding portion 65 whereby the two outer surrounding portions 65 together extend at least 360° around the axis 25 and are spaced outward from the periphery of the lens body. The ends 63 of the two haptic members 53 are joined to the periphery 27 of the lens body 21 at positions approximately 180° apart. Each of the outer surrounding portions 65 has an outer end portion 67 which overlaps the adjacent inner portion 65A of the other haptic member such that the adjacent inner portion 65A are located between the outer end portions 67 respectively and the axis 25 and hence the periphery 27 of the lens body. Each of the ends 67A of the outer end portions 67 of the two haptic members 53 has a coupling loop 41 connected thereto with an opening 43 extending therethrough. The adjacent inner portion 65A of the other haptic member extends freely through the opening 43 of each loop 41 such that the outer end portions 67 may move along the adjacent inner portion 65A to expand or decrease the dimension of the circumference of the surrounding portion 65—65, of the haptic which forms the peripheral contacting portion of the lens when inserted into the eye and holds the lens body centrally in place in the eye. Each of the loops 41 has a slit 45 as shown in FIG. 4 for receiving the adjacent inner portion of the other haptic member.

Figure 6:
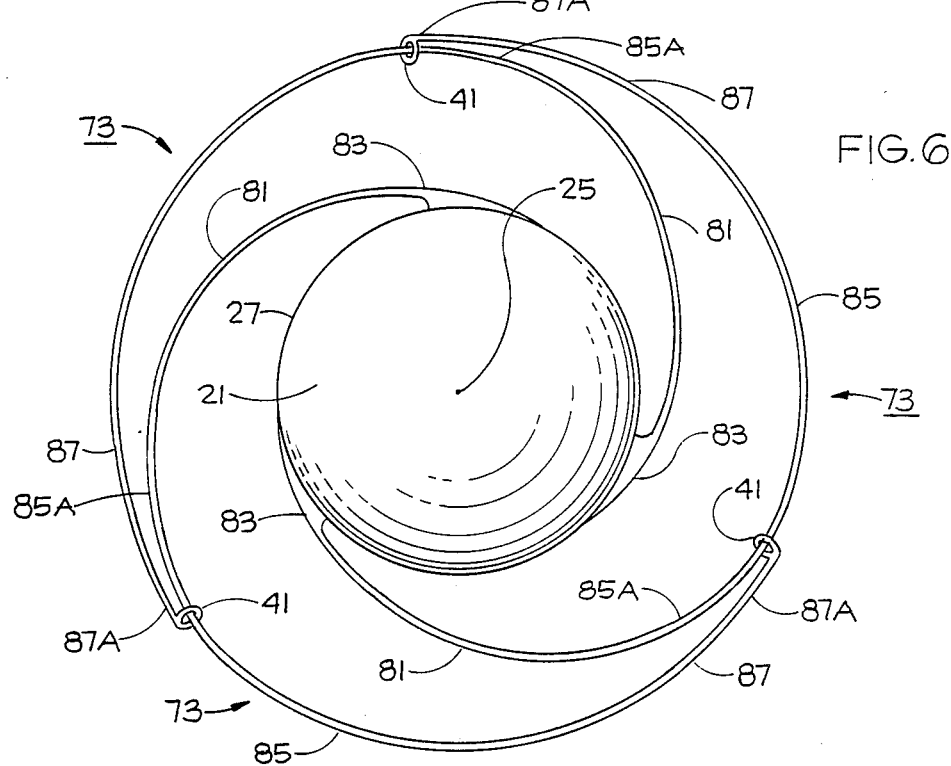
FIG. 6 is a plan view of still another embodiment of the invention wherein the lens has three haptic members.

Referring now to FIG. 6, the intraocular lens comprises a lens body 21 having three identical haptic members 73. In FIG. 6, like components are identified by like reference numerals as disclosed in FIG. 1. The three haptic members 73 each comprises an inner connecting portion 81 having an inner end 83 coupled to periphery 27 of the lens body 21 and extending outward to an outer surrounding portion 85 whereby the three outer surrounding portions 85 together extend at least 360° around the axis 25 and are spaced outward from the periphery of the lens body. The ends 83 of the three haptic members 73 are joined to the periphery 27 of the lens body 21 at positions such that adjacent ends 83 are about 120° apart. Each of the outer surrounding portions 85 has an outer end portion 87 which overlaps the adjacent inner portion 85A of an adjacent haptic member such that the adjacent inner portions 85A are located between the outer end portions 87 respectively and the axis 25 and hence the periphery 27 of the lens body. Each of the ends 87A of the outer end portions 87 of the three haptic members 73 has a coupling loop 41 connected thereto with an opening 43 extending therethrough. The adjacent inner portion 85A of the adjacent haptic member extends freely through the opening 43 of each loop 41 such that the outer end portions 87 may move along the adjacent inner portions 85A to expand or decrease the dimension of the circumference of the surrounding portions 85—85—85, of the haptic which forms the peripheral contacting portion of the lens when inserted into the eye and holds the lens body centrally in place in the eye. Each of the loops 41 has a slit 45 as shown in FIG. 4 for receiving the adjacent inner portion of the adjacent haptic member.

Referring now to FIG. 7, the intraocular lens comprises a lens body 21 having two identical haptic members 103. In FIG. 7, like components are identified by like reference numerals as disclosed in FIG. 1. The two haptic members 103 each comprises an inner connecting portion 121 having an inner end 123 joined to the periphery 27 of the lens body 21 and extending outward to an outer surrounding portion 125 whereby the two outer surrounding portions 125 together extend at least 360° around the axis 25 and are spaced outward from the periphery of the lens body. The ends 123 of the two haptic members 103 are joined to the periphery 27 of the lens body 21 as positions about 180° apart. Each of the outer surrounding portions 125 has an outer end portion 127 which overlaps the adjacent inner portion 125A of the other haptic members such that the adjacent inner portions 125A are located between the outer end portions 127 respectively and the axis 25 and hence the periphery 27 of the lens body. Between portions 121 and 125A of each haptic member there is an elbow 124 such that the haptic member doubles back on itself as its extends outward in a manner similar to that shown in U.S. Pat. No. 4,418,431. Each of the ends 127A of the outer end portions 127 of the two haptic members 103 has a coupling loop 41 connected thereto with an opening 43 extending therethrough. The adjacent inner portion 125A of the other haptic member extends freely through the opening 43 of each loop 41 such that the outer end portion 127 may move along the adjacent inner portion 125A to expand or decrease the dimension of the circumference of the surrounding portion 125—125 of the haptic which forms the peripheral contacting portion of the lens when inserted into the eye and holds the lens body centrally in place in the eye. Each of the loops 41 has a slit 45 as shown in FIG. 4 for receiving the adjacent inner portion of the other haptic member.

Figure 9:
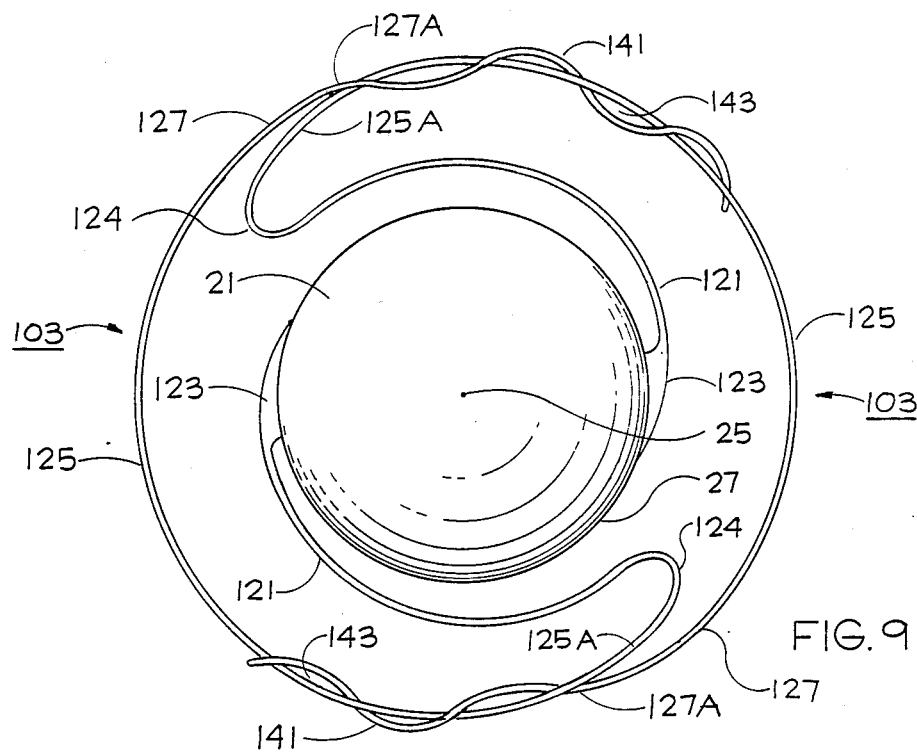
FIG. 9 is a plan view of a lens with two haptic members having configurations similar to that of FIG. 7 but with different coupling structure at the ends of the haptic members.
Figure 11:
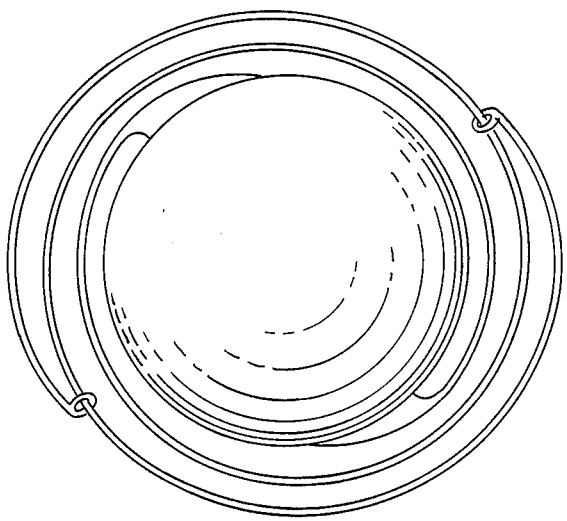
FIG. 11 illustrates the lens of FIG. 5 with its haptic members in a compressed configuration.

Referring to FIG. 9, the lens and the haptic members are the same as that disclosed in FIG. 7 except instead of having the coupling loops 41 formed at the ends 127A of the end portions 127, the ends 127A are formed into generally wound configurations 141 each defining a passage 143 with the adjacent inner portions 125A extending therethrough such that the outer end portions 127 may move along the adjacent inner portions 125A to expand or decrease the dimension of the circumference of the surrounding portions 125—125 of the haptic.

Figure 10:
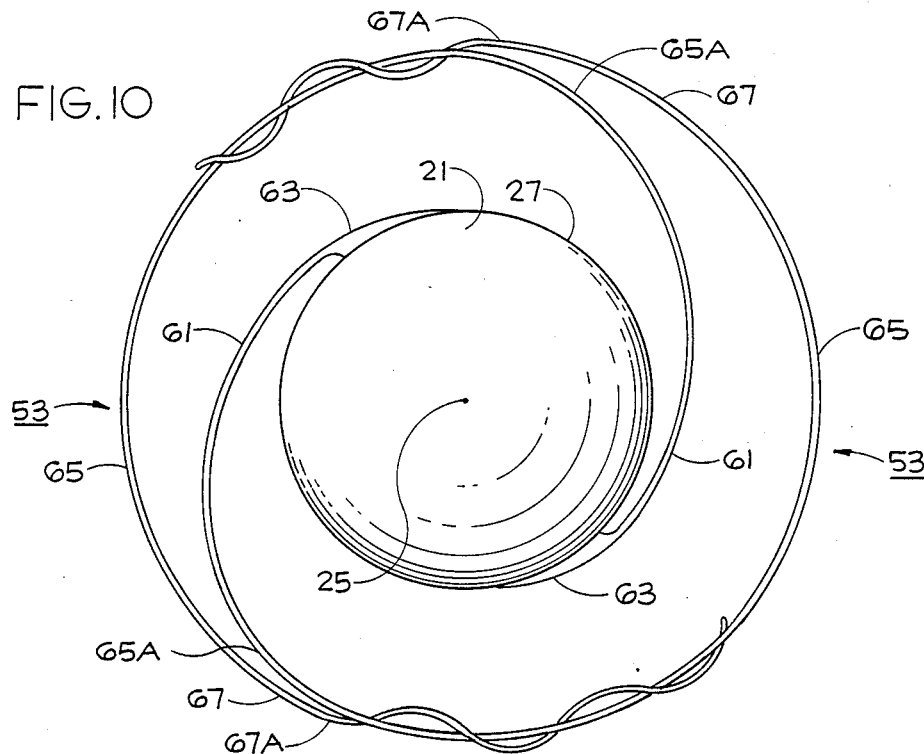
FIG. 10 is a plan view of a lens with two haptic members having configurations similar to that of FIG. 6 but employing the coupling structure of the haptics of FIG. 9.

The lens and haptic members of FIG. 10 are the same as that of FIG. 5 except that the ends 67A of the outer end portions 67 of the two haptic members 53 are formed into generally wound or twisted configurations 141 each defining a passage 143 with the adjacent inner end portions 65A extending therethrough whereby the outer end portions 67 may move along the adjacent inner portions 65A to expand or decrease the dimension of the circumference of the surrounding portions 65—65. The ends of the twisted portions 141 will be rounded to prevent scratching of the tissue of the eye.

Figure 12:
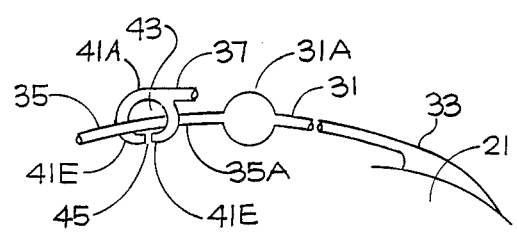
FIG. 12 is another embodiment of a coupling loop with an enlargement of the haptic member to limit sliding movement of the loop toward the optic.

Referring to FIG. 12, the coupling loop 41 is similar to that of FIG. 4 except it has been modified on that the gap edges 41E are angulated inward to allow passage of the haptic member 35 into the opening 43 prevents the haptic 35 from passing out of the opening 32. The haptic portion 31 has an enlarged portion 31A to prevent the loop 41 from sliding too far back toward the optic 21.

Figure 13:
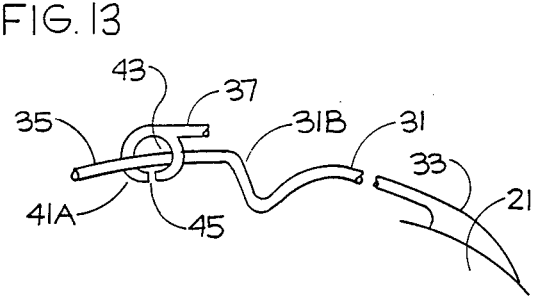
FIG. 13 illustrates the coupling loop of FIG. 12 with a change in curvature of the haptic member to limit sliding movement of the loop toward the optic.

In FIG. 13, the haptic portion 31 has a change of curvature at 31B to prevent the loop 41A from sliding too far back toward the optic 21.

In the embodiments of FIGS. 12 and 13 the haptic enlargement 31A or change of curvature 31B will be located at a desired position spaced from the optic 21 depending on the maximum circumference of the haptic desired. In FIGS. 12 and 13, the haptic member 35 is shown in broken form although it is to be understood it will be encircling as in FIG. 1.

Each of the coupling loops 41 of FIGS. 5-8 and 11 may be in the form shown at 41A in FIGS. 12 and 13. Each of the haptic members of FIGS. 5-11 may have an enlargement 31A or change of curvature 31B at its inner portion spaced a desired position from the optic 21 depending on the maximum circumference of the haptic desired.

Figure 14:
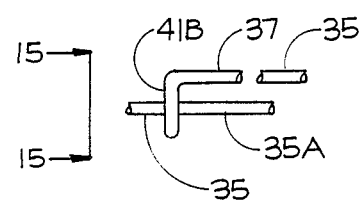
FIG. 14 is another embodiment of a coupling loop.
Figure 15:
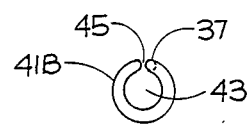
FIG. 15 is a view of FIG. 14 taken along the lines 15—15 thereof.
Figure 16:
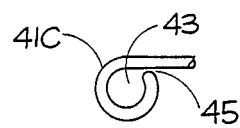

In FIGS. 1-8 and 11, the plane of the coupling loops 41, 41A are in the plane of the haptic members, however, the plane of the coupling loops can be in a plane different from that of the haptic members such as shown in FIGS. 14 and 15. In FIGS. 14 and 15, the coupling loop 41B is in a plane perpendicular to the plane of the haptic member. The loop 41B is formed as a continuation of the haptic portion 37 with its free end 41FE looping around and extending close to the haptic portion 37 forming the gap 45. The coupling loop 41C of FIG. 16 is formed in a similar manner but its plane is in the plane of the haptic. The coupling loop 41D of FIG. 17 is formed in a different manner with its plane in the plane of the haptic and with its gap 45 facing outward.

Instead of having the coupling loop or loops joined to the haptic member or members, the coupling loop or loops may be separate from the haptic member or members.

In the embodiments disclosed above, the haptic is in the plane of the optic, however, it is to be understood that the haptic may be vaulted such that the plane of its outer portion is substantially parallel with the plane of the optic but out of the plane of the optic.

The lenses and their haptics may be formed of polymethylemethacrylate, prolene, (polypropylene) or other suitable materials.

I claim:

1. An intraocular insert suitable for use as an artificial lens implant in a human eye, comprising:
   a lens body having a central axis and an outer periphery,
   haptic means for supporting said lens body in a human eye,
   said haptic means comprising a surrounding portion adapted to engage the tissue of a human eye,
   said surrounding portion extending at least 360° around said axis and being spaced outward from said periphery of said lens body, said haptic means comprising at least one inner connecting portion having an inner end joined to said periphery of said lens body and extending outward to said surrounding portion, said surrounding portion comprising at least one outer portion having an outer end portion and an adjacent portion located between said outer end portion and said axis, coupling means for coupling said outer end portion and said adjacent portion together such that said outer end portion may be moved along said adjacent portion to decrease or expand the circumference of said surrounding portion of said haptic means.

2. The intraocular insert of claim 1, wherein said coupling means is joined to said outer end portion.

3. The intraocular insert of claim 2, wherein said coupling means has an opening with said adjacent portion extending into said opening.

4. The intraocular insert of claim 2, wherein said coupling means comprises a loop with said adjacent portion extending through said loop.

5. The intraocular insert of claim 4, wherein said coupling means comprises said outer end portion formed into a generally wound or twisted configuration defining a passage with said adjacent portion extending through said passage.

6. The intraocular insert of claim 1, wherein:

said haptic means comprises a single haptic member comprising said inner connecting portion having said inner end joined to said periphery of said lens body and extending outward and then around said axis forming said surrounding portion of said haptic means and having said outer portion with its said outer end portion.

7. The intraocular insert of claims 6, wherein said coupling means is joined to said outer end portion of said outer portion.

8. The intraocular insert of claim 6, wherein said coupling means has an opening with said adjacent portion extending into said opening.

9. The intraocular insert of claim 7, wherein said coupling means comprises a loop with said adjacent portion extending through said loop.

10. The intraocular insert of claim 7, wherein said coupling means comprises said outer end portion having a generally wound or twisted configuration defining a passage with said adjacent portion extending through said passage.

11. The intraocular insert of claim 1, wherein:

said haptic means comprises at least two haptic members, each of said haptic members comprising an inner connecting portion having an inner end joined to said periphery of said lens body and extending outward and then partially around said axis for forming said surrounding portion of said haptic means and having an outer portion with an outer end portion with an adjacent portion of the other haptic member, located between said outer end portion and said axis, coupling means for coupling each of said outer end portions and its associated adjacent portion together such that said outer end portions may be moved along said adjacent portions to decrease or expand the circumference of said surrounding portion of said haptic means, said inner ends of said haptic members being joined to said periphery of said lens body at spaced apart positions, said coupling means being located along said surrounding portion of said haptic means at spaced apart positions.

12. The intraocular insert of claim 11, wherein said coupling means are joined to said outer end portions of said outer portions.

13. The intraocular insert of claim 12, wherein each of said coupling means has an opening with each of said adjacent portions extending into one of said openings.

14. The intraocular insert of claim 12, wherein each of said coupling means comprises a loop with its associated adjacent portion extending through said loop.

15. The intraocular insert of claim 12, wherein said coupling means comprises said outer end portions having generally wound or twisted configurations defining passages with said adjacent portions extending through said passages.

16. The intraocular insert of claim 1, wherein:

said haptic means comprises three haptic members, each of said haptic members comprising an inner connecting portion having an inner end joined to said periphery of said lens body and extending outward and then partially around said axis for forming said surrounding portion of said haptic means and having an outer portion with an outer end portion with an adjacent portion of an adjacent haptic member, located between said outer end portion and said axis, coupling means for coupling each of said outer end portions and its associated adjacent portion together such that said outer end portions may be moved along said adjacent portions to decrease or expand the circumference of said surrounding portion of said haptic means, said inner ends of said haptic members being joined to said periphery of said lens body at spaced apart positions, said coupling means being located along said surrounding portion of said haptic means at spaced apart positions.

17. The intraocular insert of claim 16, wherein said coupling means are joined to said outer end portions of said outer portions.

18. The intraocular insert of claim 17, wherein each of said coupling means has an opening with each of said adjacent portions extending into one of said openings.

19. The intraocular insert of claim 17, wherein each of said coupling means comprises a loop with its associated adjacent portion extending through said loop.

20. The intraocular insert of claim 17, wherein said coupling means comprises said outer end portions having generally wound or twisted configurations defining passages with said adjacent portions extending through said passages.

* * * * *